(12) United States Patent
Arisaka

(10) Patent No.: US 7,644,615 B2
(45) Date of Patent: Jan. 12, 2010

(54) HUMIDITY SENSOR HAVING HUMIDITY SENSITIVE FILM AND METHOD FOR MANUFACTURING THE SAME

(75) Inventor: Naoki Arisaka, Kariya (JP)

(73) Assignee: DENSO CORPORATION, Kariya (JP)

( * ) Notice: Subject to any disclaimer, the term of this patent is extended or adjusted under 35 U.S.C. 154(b) by 499 days.

(21) Appl. No.: 11/589,947

(22) Filed: Oct. 31, 2006

(65) Prior Publication Data

US 2007/0113648 A1 May 24, 2007

(30) Foreign Application Priority Data

Nov. 7, 2005 (JP) ............... 2005-322887

(51) Int. Cl.
*G01N 27/22* (2006.01)

(52) U.S. Cl. ................................. 73/335.04

(58) Field of Classification Search ............. 73/355.04, 73/39.01, 25.04, 29.01
See application file for complete search history.

(56) References Cited

U.S. PATENT DOCUMENTS 6,580,600 B2   6/2003   Toyoda et al.
6,834,547 B2*  12/2004  Chen et al. ............... 73/335.02
2002/0114125 A1  8/2002   Toyoda et al.
2006/0032290 A1*  2/2006  Liu ........................... 73/29.02
2006/0048572 A1*  3/2006  Isogai et al. ............. 73/335.04
2006/0096371 A1*  5/2006  Isogai et al. ............. 73/335.04
2008/0148842 A1*  6/2008  Oda ......................... 73/204.26
2008/0163687 A1*  7/2008  Kranz et al. ............. 73/514.32

FOREIGN PATENT DOCUMENTS

| JP | A-6-118045   | 4/1994 |
| JP | A-2002-71612 | 3/2002 |
| JP | A-2002-181754| 6/2002 |

* cited by examiner

*Primary Examiner*—John Fitzgerald
(74) *Attorney, Agent, or Firm*—Posz Law Group, PLC

(57) ABSTRACT

A humidity sensor includes: a sensor chip including a capacitive humidity sensor element and a connection electrode, wherein the capacitive humidity sensor element includes a humidity sensitive film having relative permittivity changeable in accordance with humidity, and wherein the connection electrode is electrically connected to the humidity sensor element; a lead plate electrically connected to the connection electrode; and a mold for covering a connection portion between the connection electrode and the lead plate. The mold is disposed on the sensor chip and includes a groove. The humidity sensitive film is disposed in the groove. The humidity sensitive film has a height in the groove, the height equal to or lower than a surface of the mold. The height of the humidity sensitive film in the groove is homogeneous.

4 Claims, 3 Drawing Sheets

HUMIDITY SENSOR HAVING HUMIDITY SENSITIVE FILM AND METHOD FOR MANUFACTURING THE SAME

CROSS REFERENCE TO RELATED APPLICATION

This application is based on Japanese Patent Application No. 2005-322887 filed on Nov. 7, 2005, the disclosure of which is incorporated herein by reference.

FIELD OF THE INVENTION

The present invention relates to a humidity sensor having a humidity sensitive film and a method for manufacturing the same.

BACKGROUND OF THE INVENTION

Conventionally, a capacitive humidity sensor having a humidity sensitive film is disclosed in, for example, U.S. Pat. No. 6,580,600. The relative permittivity of the humidity sensitive film is changeable in accordance with humidity. The humidity sensitive film is disposed between a pair of electrodes.

In the sensor, the electrodes are disposed on the same plan of a substrate, and face each other. The humidity sensitive film is disposed between the electrodes and covers the electrodes.

In a manufacturing method of the above sensor, a paste including high polymer material is printed on the substrate by a screen printing method, and then, the paste is hardened so that the humidity sensitive film is formed. In this case, a step of patterning the humidity sensitive film is not necessary, compared with a spin coating method for coating the humidity sensitive film on the substrate. Thus, the manufacturing method including the screen printing step is simplified.

In the above sensor, a pair of electrodes provides a capacitor including the humidity sensitive film as a dielectric layer between the electrodes. On the basis of the capacitance change of the capacitor, the humidity sensor detects the humidity. In this case, the capacitance is affected by not only the humidity sensitive film between the electrodes but also the humidity sensitive film on the electrodes. The capacitance derived from the humidity sensitive film on the electrodes is a fringing capacitance. Further, an initial capacitance of the above sensor is comparatively small, compared with a parallel plate type sensor. Thus, the sensitivity of the above sensor is much affected by thickness deviation of the humidity sensitive film.

Here, when the humidity sensitive film is formed by the screen printing method, the thickness of the humidity sensitive film depends on a physical condition of the paste such as viscosity, a condition of the surface of the substrate such as wettability of the paste, a screen printing condition such as dimensions of an opening of the pattern, i.e., an opening degree of a screen, a thickness of emulsion and a screen tension, and a squeegee condition such as a scanning speed and a printing pressure. Specifically, the thickness of a part of the humidity sensitivity film around a periphery of the opening of the pattern and near a screen mesh is much deviated from a desired thickness.

SUMMARY OF THE INVENTION

In view of the above-described problem, it is an object of the present disclosure to provide a humidity sensor having a humidity sensitive film. It is another object of the present disclosure to provide a method for manufacturing a humidity sensor having a humidity sensitive film.

According to a first aspect of the present disclosure, a humidity sensor includes: a sensor chip including a capacitive humidity sensor element and a connection electrode, wherein the capacitive humidity sensor element includes a humidity sensitive film having relative permittivity changeable in accordance with humidity, and wherein the connection electrode is electrically connected to the humidity sensor element; a lead plate electrically connected to the connection electrode; and a mold for covering a connection portion between the connection electrode and the lead plate. The mold is disposed on the sensor chip and includes a groove. The humidity sensitive film is disposed in the groove of the mold. The humidity sensitive film has a height in the groove, the height equal to or lower than a surface of the mold. The height of the humidity sensitive film in the groove is homogeneous.

In the above sensor, since the height of the humidity sensitive film in the groove is homogeneous, the thickness of the humidity sensitive film is also homogeneous. Accordingly, thickness variation of the humidity sensitive film is small, so that variation of sensor sensitivity is reduced. Further, the above groove provides a dam structure for accommodating the humidity sensitive film, so that a manufacturing cost of the sensor is reduced. Furthermore, since the humidity sensitive film is exposed from the mold, the sensor sensitivity is improved.

According to a second aspect of the present disclosure, a method for manufacturing a humidity sensor includes: forming a pair of capacitance electrodes and a connection electrode on a substrate, wherein the capacitance electrodes are separated each other by a predetermined distance and face each other, and wherein the connection electrode is electrically connected to the capacitance electrodes; connecting the connection electrode to a lead plate; molding a connection portion between the connection electrode and the lead plate with a mold, wherein the mold includes a groove, which reaches the capacitance electrodes on the substrate; and forming a humidity sensitive film in the groove so that the humidity sensitive film covers the capacitance electrodes, wherein the humidity sensitive film has relative permittivity changeable in accordance with humidity.

In the above method, the humidity sensitive film is easily formed in the groove without forming an additional dam structure. Thus, the manufacturing cost of the sensor is reduced. Further, the humidity sensitive film is easily arranged at a predetermined position, i.e., in the groove, and the height of the humidity sensitive film in the groove is easily uniformed. Thus, the thickness variation of the humidity sensitive film is reduced, so that sensor sensitivity variation is reduced.

Alternatively, the method may further include forming a through hole in the mold. The humidity sensitive film has a height in the groove, the height lower than a surface of the mold. The through hole penetrates from an outer surface of the mold to a side wall of the groove. The through hole in the mold is disposed between the surface of the mold and a surface of the humidity sensitive film in the groove. Further, the forming the through hole may be performed together with the molding the connection portion with the mold in such a manner that a molding form provides the though hole and the mold, and the forming the humidity sensitive film in the groove may be performed to lower the height of the humidity sensitive film than the through hole.

According to a third aspect of the present disclosure, a humidity sensor includes: a substrate; a capacitive humidity sensor element disposed on a first surface of the substrate, wherein the capacitive humidity sensor element includes a humidity sensitive film having relative permittivity changeable in accordance with humidity; and a mold for covering the substrate. The mold includes a groove so that the groove reaches the first surface of the substrate. The humidity sensitive film is disposed in the groove. The humidity sensitive film has a top surface in the groove. The top surface of the humidity sensitive film is equal to or lower than a top surface of the mold, and the top surface of the humidity sensitive film in the groove is homogeneous.

In the above sensor, since the height of the humidity sensitive film in the groove is homogeneous, the thickness of the humidity sensitive film is also homogeneous. Accordingly, thickness variation of the humidity sensitive film is small, so that variation of sensor sensitivity is reduced. Further, the above groove provides a dam structure for accommodating the humidity sensitive film, so that a manufacturing cost of the sensor is reduced. Furthermore, since the humidity sensitive film is exposed from the mold, the sensor sensitivity is improved.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

Figure 1A:
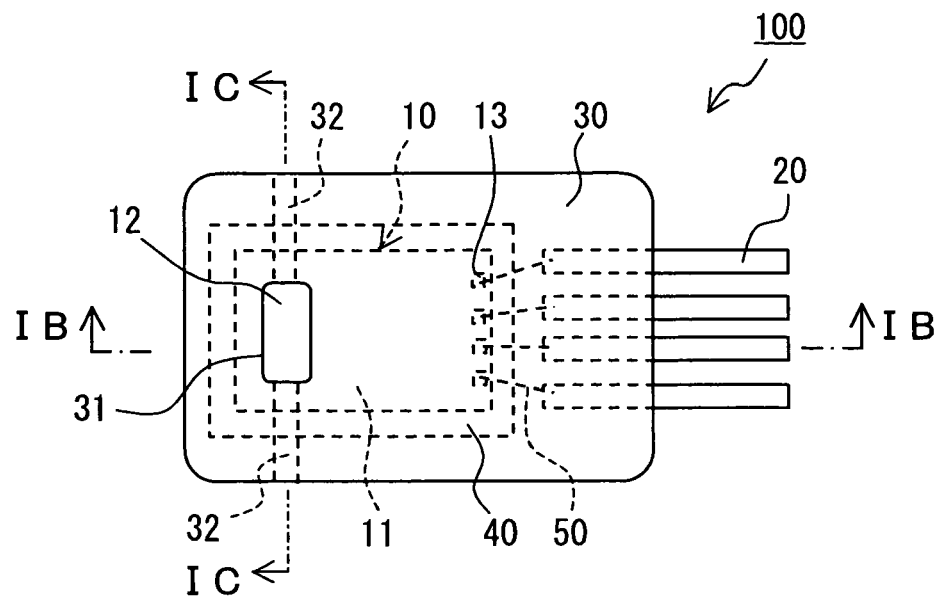
FIG. 1A is a plan view showing a humidity sensor.
Figure 1B:
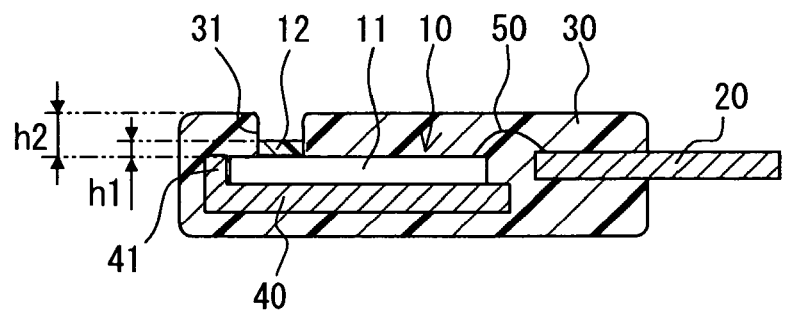
FIG. 1B is a cross sectional view showing the sensor taken along line IB-IB in FIG. 1A.
Figure 1C:
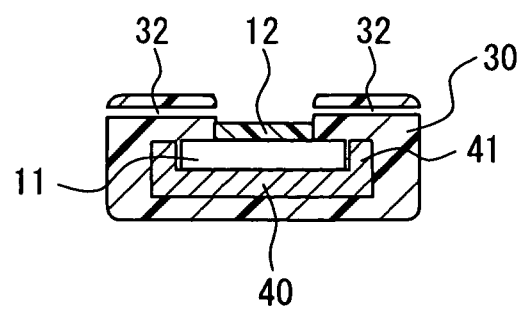
FIG. 1C is a cross sectional view showing the sensor taken along line IC-IC in FIG. 1A.

FIGS. 1A to 1C show a humidity sensor 100 according to an example embodiment. The sensor 100 includes a sensor chip 10 having a capacitive humidity sensor element, a lead plate 20 for connecting to the sensor chip 10, a mold 30 for covering the connection portion between the sensor chip 10 and the lead plate 20, and a support member 40 for mounting the sensor chip 10 thereon.

The sensor chip 10 includes a silicon substrate 11, a humidity sensitive film 12 disposed on the substrate 11, an electrode pad 13. The relative permittivity of the humidity sensitive film 12 is changeable in accordance with humidity around the sensor 100. The electrode pad 13 is connected to the humidity sensor element electrically, and functions as an external connection terminal. The electrode pad 13 is electrically connected to the lead plate 20 through a bonding wire 50 so that a signal detected by the humidity sensor element is outputted to an external circuit through the lead plate 20. The lead plate 20 is made of conductive material.

Figure 2A:
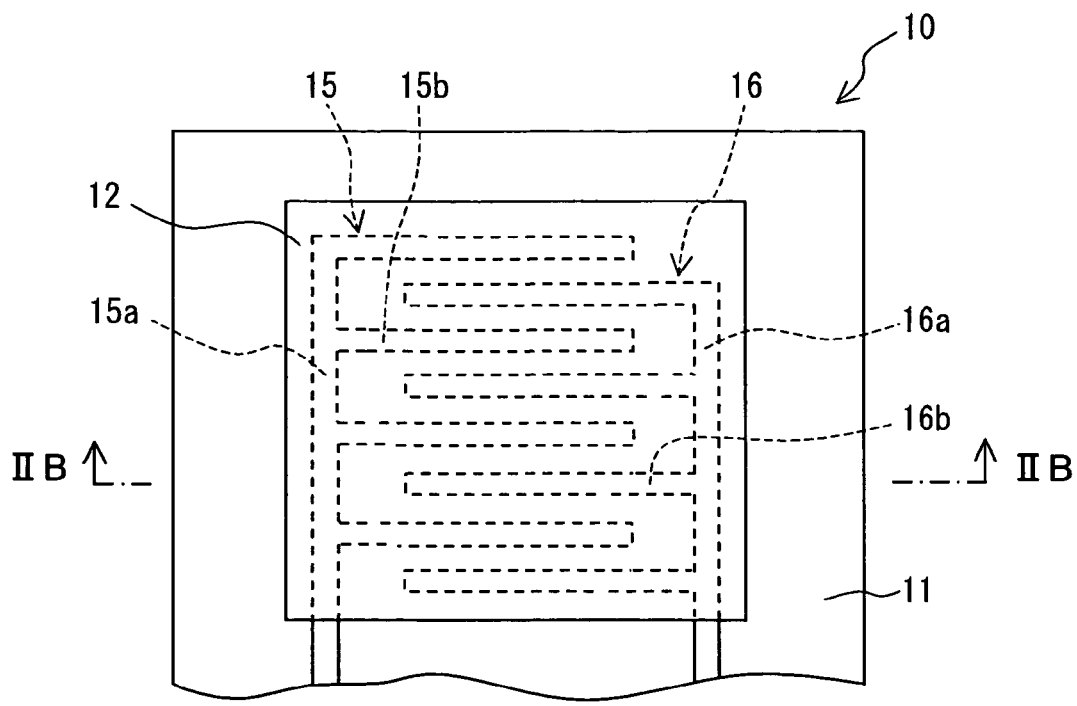
FIG. 2A is a partial plan view showing a sensor chip in the sensor.
Figure 2B:
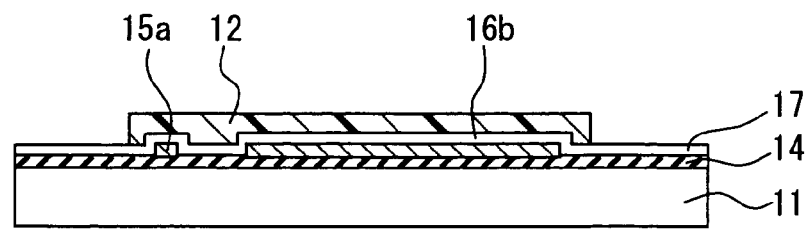
FIG. 2B is a cross sectional view showing the sensor chip taken along line IIB-IIB in FIG. 2A.

The humidity sensor element in the sensor chip 10 is shown in FIGS. 2A and 2B. As shown in FIG. 2B, an insulation film 14 made of oxide silicon is formed on the substrate 11. A pair of electrodes 15, 16 is formed on the insulation film 14. The electrodes 15, 16 face each other, and the first electrode 15 is separated from the second electrode 16 by a predetermined distance. The electrodes 15, 16 provide capacitance electrodes.

As shown in FIG. 2A, each electrode 15, 16 includes a common electrode portion 15a, 16a and a comb-teeth electrode portion 15b, 16b. The comb-teeth electrode portion 15b, 16b protrudes from the common electrode portion 15a, 16a toward one direction. The comb-teeth electrode portion 15b, 16b includes multiple comb teeth electrodes such as four comb teeth electrodes in FIG. 2A. The comb-teeth electrode portions 15b, 16b in the electrodes 15, 16 are interleaved each other so that a pair of capacitance electrodes is formed.

Thus, since the capacitance electrodes 15, 16 have a comb-teeth shape, the planar area of the capacitance electrodes 15, 16 can be minimized. Further, a capacitance area between the electrodes 15, 16 is maximized. The capacitance area is provided by a facing area of each electrode 15, 16, a facing area of each comb-teeth electrodes. Thus, the capacitance between the capacitance electrodes 15, 16 is much changeable in accordance with the humidity change around the sensor 100. Thus, the sensor sensitivity of the sensor 100 is improved.

Each electrode 15, 16 is formed such that a low resistance metallic film such as an aluminum film, a gold film, and a Pt film is formed on the substrate 11 by using an vapor deposition method or a sputtering method. Then, the metallic film is patterned by using a photo lithography method so that the metallic film is patterned to have a comb-teeth pattern. In FIG. 2A, the electrode 15, 16 is made of aluminum.

A protection film 17 made of, for example, silicon nitride film is formed on the substrate 11 such that the protection film 17 covers the electrodes 15, 16 and a space between the electrodes 15, 16. The protection film 17 is deposited on the substrate 11 by using a plasma CVD method or the like. The thickness of the protection film 17 on each part of the substrate 11 is constant. The protection film 17 protects the electrodes 15, 16 from being eroded by moisture. When the electrodes 15, 16 have sufficient moisture proof, the sensor 100 may not have the protection film 17.

Each electrode 15, 16 is electrically connected to the electrode pad 13 through a wire (not shown) so that the electrode 15, 16 is connected to a signal processing circuit, a compensation circuit and the like through the pad 13 and the lead plate 20. The signal processing circuit detects capacitance change of the capacitor, and the compensation circuit compensates an output of the capacitor. It is required for the pad 13 to expose outside in order to connect to the bonding wire 50. Accordingly, the pad 13 is not covered with the protection film 17. Further, when the substrate is made of semiconductor substrate, the compensation circuit and the signal processing circuit may be integrated into one substrate.

A humidity sensitive film 12 is formed on the protection film 17 in such a manner that the humidity sensitive film 12 covers the capacitance electrodes 15, 16 and a space between the electrodes 15, 16. The humidity sensitive film 12 is formed such that varnish poly amide acid is applied on the protection film 17. The varnish poly amide acid is preliminarily processed to have a predetermined viscosity, and the varnish poly amide acid is a precursor of poly imide. Then, the poly amide acid is heated up to a predetermined temperature so that the poly amide acid is ring-closed. Thus, the poly amide acid is changed to the imide.

In the humidity sensor 100, when the moisture penetrates into the humidity sensitive film 12, the relative permittivity of the humidity sensitive film 12 is changed in accordance with the moisture penetrated into the humidity sensitive film 12, since the moisture has a large relative permittivity, compared with the humidity sensitive film 12. As a result, the capacitance of the capacitor provided by the capacitance electrodes 15, 16 and the humidity sensitive film 12 is changed.

The moisture in the humidity sensitive film 12 corresponds to the humidity around the sensor 100. Thus, the humidity is detected by the capacitance change of the capacitor.

The mold 30 is made of electrically insulation material such as epoxy resin. The insulation material is capable of integrally forming. The mold 30 integrally molds the bonding wire 50 and connection portions among the bonding wire 50, the pad 13 and the lead plate 20 after the sensor chip 10 is mounted on the sensor chip 10. In the sensor 100, the construction of the mold 30 has a specific characteristic.

The support member 40 supports the sensor chip 10. The support member 40 is made of the same material as the lead plate 20 and formed by an etching method or a press working method. When the support member 40 is made of the same material as the lead plate 20, the manufacturing method of the sensor 100 is simplified. As shown in FIGS. 1B and 1C, a positioning member 41 protrudes from a mounting surface of the support member 40, the mounting surface on which the sensor chip 10 is mounted. Specifically, the positioning member 41 protrudes upward, and faces a side of the sensor chip 10. Thus, the sensor chip 10 is positioned at a predetermined position on the support member with reference to the positioning member 41 as a positioning reference. The backside of the sensor chip 10, which is opposite to the humidity sensor element, is mounted on the support member 40. The sensor chip 10 is bonded to the support member 40 with adhesive or the like. Although the sensor 100 includes one support member 40, the sensor may have multiple support members.

In the sensor 100, a part of the humidity sensitive film 12 provides a dielectric member, and the first and second electrodes 15, 16 together with the part of the humidity sensitive film 12 provide a capacitor. The humidity sensor 100 detects humidity based on capacitance change of the capacitor. At this time, the capacitance change is affected by not only the part of the humidity sensitive film 12 disposed between two electrodes 15, 16 but also another part of the humidity sensitive film 12 disposed above the electrodes 15, 16. The capacitance from the other part of the humidity sensitive film 12 is a fringing capacitance. Further, since the sensor 100 includes the comb-teeth electrode portions 15b, 16b, an initial capacitance of the sensor 100 is comparatively small, compared with a parallel plate type humidity sensor. Thus, the sensitivity of the sensor may be affected by thickness variation of the humidity sensitive film 12.

However, in the sensor 100, the mold 30 covers the connection portion between the pad 13 and the lead plate 20. Further, the mold 30 is disposed on the sensor chip 10 so that the mold 30 contacts all side surfaces of the humidity sensitive film 12. Accordingly, the mold 30 surrounds a periphery of the humidity sensitive film 12. Specifically, the sensor 100 includes a groove 31, which is disposed in the mold 30, and surrounds the humidity sensitive film 12. The bottom of the groove 31 is provided by the sensor chip 10. Thus, the groove 31 with the sensor chip 10 provides a dam structure. The humidity sensitive film 12 is disposed on a predetermined region, which is defined by the groove 31 and the sensor chip 10. The humidity sensitive film 12 has a surface height h1 from the silicon substrate 11, and the height h1 of the film 12 is lower than a height h2 of the mold 30. The height h1 of the film 12 is substantially uniform.

The height h1 of the humidity sensitive film 12 from the surface of the substrate 11 is homogeneous, so that the thickness variation of the humidity sensitive film 12 above the electrodes 15, 16 is reduced. Accordingly, the sensitivity of the sensor 100 is improved. Specifically, variation of sensitivity in each sensor 100 is reduced.

Further, since the humidity sensitive film 12 in the humidity sensor element is exposed from the mold 30, the sensitivity of the sensor 100 is improved, compared with a case where a protection gel film covers whole of a humidity sensor element.

The height h2 of the mold 30 from the surface of the substrate 11 is higher than the height h1 of the humidity sensitive film 12, and a through hole 32 is formed between a portion of a sidewall of the groove 31 higher than the surface of the humidity sensitive film 12 and another sidewall of the mold 30. Specifically, the sidewall of the groove 31 provides a contact surface to the humidity sensitive film 12. The other sidewall of the mold 30 provides an outer surface of the mold 30. The height h2 of the mold 30 is higher than the height h1 of the humidity sensitive film 12. Thus, even when the mold 30 has a concavity formed by the groove 31 and the surface of the humidity sensitive film 12, gas does not stay in the concavity. The gas in the concavity can flow through the through hole 32. Accordingly, the humidity around the sensor 100 can be detected accurately. The through hole 32 connects the sidewall of the mold 30 and the sidewall of the groove 31. In FIG. 1A, the sensor 100 includes two through holes 32. However, the sensor 100 may include multiple through holes.

Figure 3A:
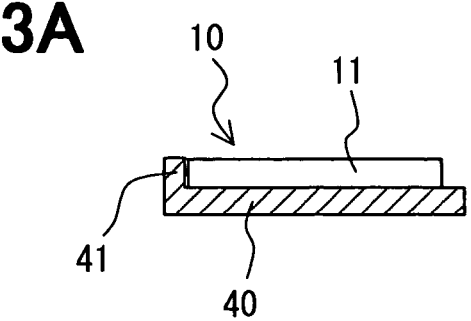
FIGS. 3A to 3D are cross sectional views showing a manufacturing process of the sensor shown in FIG. 1A.

The manufacturing method of the sensor 100 is explained with reference to FIGS. 3A to 3D. FIG. 3A represents a mounting step, FIG. 3B represents a connection step, FIG. 3C represents a mold step, and FIG. 3D represents a forming step of the humidity sensitive film 12.

Firstly, the sensor chip without the humidity sensitive film 12 is prepared. In this preparation step, construction of the humidity sensor element without the humidity sensitive film 12 is formed, and the pad 13 connected to the electrodes 15, 16 is formed.

Then, the sensor chip 10 is mounted on the support member 40 in such a manner that the backside of the sensor chip 10 opposite to the humidity sensor element is disposed on the support member 40. Thus, the backside of the sensor chip 10 provides a mounting surface of the chip 10. At this time, the sensor chip 10 is positioned with reference to the positioning member 41 disposed on the support member 40. Further, the sensor chip 10 is bonded to the support member 40. This is a mounting step.

Figure 3B:
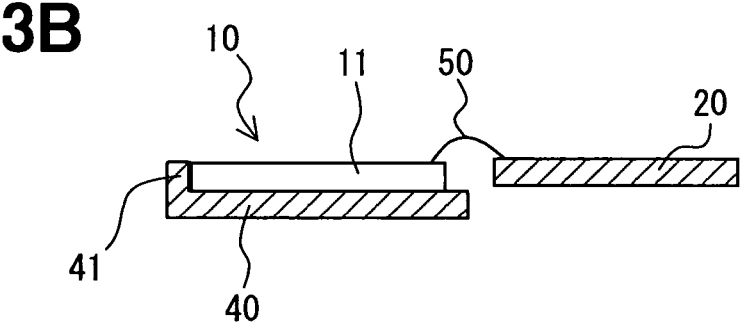
Figure 3C:
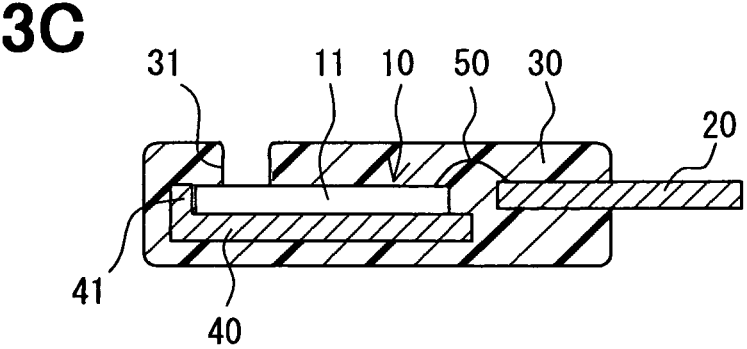
Figure 3D:
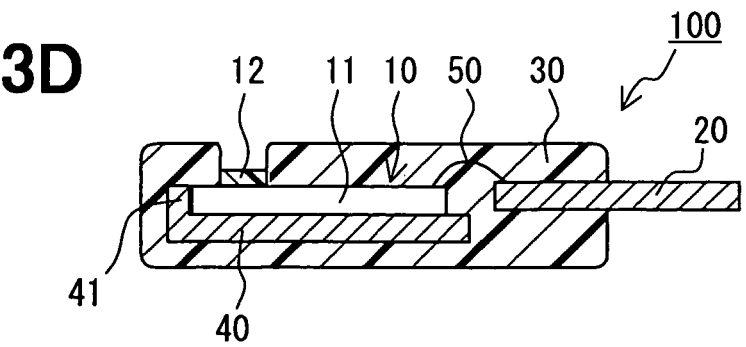

Then, as shown in FIG. 3B, the pad 13 of the sensor chip 10 is electrically connected to the lead plate 20 with the bonding wire 50. Then, molding material is injected in a die for the mold 30 not shown so that the mold 30 is formed by an insert molding method. In this case, the bonding wire 50 and a connection between the pad and the lead plate 20 are sealed with the mold 30. Further, the mold 30 surrounds a humidity-sensitive-film-to-be-formed portion on the substrate 11. This is the molding step.

Thus, the groove 31 in the mold 30 having the bottom of the sensor chip 10 is formed in such a manner that the groove 31 surrounds the humidity-sensitive-film-to-be-formed portion. The groove 31 defines the humidity-sensitive-film-to-be-formed portion on the substrate 11, and further, the groove 31 functions as a dam of the humidity sensitive film 12. Further, in the molding step, the through hole 32 is also formed in the mold 30.

Then, a material for the humidity sensitive film 12 is inserted into the groove 31, which is surrounded with the mold 30. Here, the material of the humidity sensitive film 12 is, for example, humidity sensitive film precursor liquid solution having viscosity equal to or smaller than 10 Pa·s. Then, the material is hardened, so that the humidity sensitive film 12 is formed on the substrate in the humidity sensitive film forming step. In this case, the material is inserted into the groove 31 to have a predetermined height in the groove 31 so that the height h1 of the humidity sensitive film 12 is lower than the height h2 of the mold 30. In FIG. 3D, the material is poured into the groove 31 in such a manner that the height h1 of the humidity sensitive film 12 is equal to or lower than a lower side of the through hole 32.

In FIGS. 3A to 3D, the support member 40 is made of the same material as the lead plate 20, and further, the support member 40 and the lead plate 20 are integrated together with a frame (not shown). When the support member 40 and the lead plate 20 are integrated together, positioning accuracy in the sensor 100 including the sensor chip 10 is improved. Further, the connection step and the molding step are simplified. The frame is removed in a separation step after a curing step of the molding step and before the humidity sensitive film forming step. Alternatively, the separation step of the frame may be after the humidity sensitive film forming step. In FIG. 3A, the lead plate 20 integrated with the support member 40 is not shown. Thus, the sensor 100 is completed.

In the above manufacturing method of the sensor 100, the dam structure provided by the groove 31 having the bottom of the sensor chip 10 is formed by using the mold 30. Here, the dam structure surrounds the humidity-sensitive-film-to-be-formed portion on the substrate 11, and the mold 30 covers the connection portion between the pad 13 and the lead plate 20. The material of the humidity sensitive film 12 is poured into the groove 31 so that the humidity sensitive film 12 is formed. Accordingly, the dam structure is not additionally formed on the substrate, so that the manufacturing cost of the sensor 100 is reduced.

Since the material of the humidity sensitive film 12 is poured into the groove 31, the humidity sensitive film 12 is accurately positioned at a predetermined position, i.e., in the groove 31. Further, the height h1 of the humidity sensitive film 12 from the surface of the substrate 11 becomes homogeneous. Thus, the thickness variation of the humidity sensitive film 12 above the electrodes 15, 16 is reduced, so that the sensitivity variation in each sensor 100 is reduced. Specifically, in this method, the material of the humidity sensitive film 12 has the viscosity equal to or smaller than 10 Pa·s. Thus, the viscosity of the material is comparatively small, so that the height of the humidity sensitive film 12 becomes homogeneous sufficiently.

In the above method, the sensor chip mounted on the support member 40 is electrically connected to the lead plate 20. Alternatively, the sensor 100 may have no support member 40.

Although the height h1 of the humidity sensitive film 12 is lower than the height h2 of the mold 30, the height h1 of the humidity sensitive film 12 may be equal to the height h2 of the mold 30. In this case, the humidity sensitive film 12 completely fills the groove 31, so that no concavity composed of a top of the humidity sensitive film 12 and a sidewall of the groove 31 is formed on the substrate 11. Accordingly, the through hole 32 cannot be formed on the mold 30. However, in this case, it is not necessary to form the through hole 32, since the surface of the humidity sensitive film 12 is on the same plane as the surface of the mold 30. Thus, the gas flows sufficiently through the humidity sensitive film 12.

In the molding step, the frame provides the groove 31 and the through hole 32 in the mold 30. Alternatively, after the molding step, at least one of the groove 31 and the through hole 32 may be formed by an etching method, a laser beam processing method or the like.

In the above method, the substrate 11 is made of silicon, since the sensor chip 10 is formed by a conventional semiconductor process so that the manufacturing cost of the sensor chip 10 is low. Alternatively, the substrate 11 may be made of another material such as glass.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A humidity sensor comprising:
   a sensor chip including a capacitive humidity sensor element and a connection electrode, wherein the capacitive humidity sensor element includes a humidity sensitive film having relative permittivity changeable in accordance with humidity, and wherein the connection electrode is electrically connected to the humidity sensor element;
   a lead plate electrically connected to the connection electrode; and
   a mold for covering a connection portion between the connection electrode and the lead plate, wherein
   the mold is disposed on the sensor chip and includes a groove,
   the humidity sensitive film is disposed in the groove of the mold,
   the humidity sensitive film has a height in the groove, the height equal to or lower than a surface of the mold,
   the height of the humidity sensitive film in the groove is homogeneous, and
   the height of the humidity sensitive film is lower than the surface of the mold,
   the mold further includes a through hole, which penetrates from an outer surface of the mold to a side wall of the groove, and
   the through hole in the mold is disposed between the surface of the mold and a surface of the humidity sensitive film in the groove.

2. The sensor according to claim 1, wherein
   the humidity sensor element includes a pair of capacitance electrodes, which are arranged on a surface of the sensor chip to face each other and to be separated by a predetermined distance,
   each capacitance electrode includes a common electrode portion and a comb-teeth electrode portion protruding from one side of the common electrode portion,
   one of the comb-teeth electrode portions in a pair of capacitance electrodes interleaves the other one of the comb-teeth electrode portions, and
   the humidity sensitive film covers at least the comb-teeth electrode portions of the capacitance electrodes.

3. The sensor according to claim 1, further comprising:
   a support member for mounting the sensor chip, wherein
   the sensor chip has a mounting surface opposite to the humidity sensor element,
   the mounting surface of the sensor chip is disposed on the support member, and
   the mold molds the sensor chip with the support member.

4. The sensor according to claim 3, wherein
   the support member is made of a same material as the lead plate.

* * * * *